United States Patent
Michel et al.

(10) Patent No.: US 6,413,242 B1
(45) Date of Patent: *Jul. 2, 2002

(54) INJECTION DEVICE FOR INJECTION OF LIQUID

(75) Inventors: Peter Michel, Burgdorf; Peter Nydegger, Utzigen; Philipp Weber, Burgdorf, all of (CH)

(73) Assignee: Disetronic Licensing AG, Burgdorf (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,674
(22) PCT Filed: Jul. 5, 1996
(86) PCT No.: PCT/CH96/00248
§ 371 (c)(1), (2), (4) Date: May 21, 1998
(87) PCT Pub. No.: WO98/01171
PCT Pub. Date: Jan. 15, 1998

(51) Int. Cl.[7] .................................................. A61M 5/00
(52) U.S. Cl. ....................................... 604/187; 604/188
(58) Field of Search ........................ 604/207–211, 232, 604/234, 235, 264, 187

(56) References Cited

U.S. PATENT DOCUMENTS

| 4,592,745 A | 6/1986 | Rex et al. |
| 4,865,591 A | 9/1989 | Sams |
| 4,883,472 A | 11/1989 | Michel |

(List continued on next page.)

FOREIGN PATENT DOCUMENTS

| DE | 4112259 | 4/1991 |
| DE | 19519147 | 7/1995 |
| DK | 3638984 | 11/1986 |

(List continued on next page.)

Primary Examiner—Brian L. Casler
Assistant Examiner—Kevin C. Sirmons
(74) Attorney, Agent, or Firm—Dorsey & Whitney LLP

(57) ABSTRACT

Injection device (1) for injecting fluid from a fluid container (4) equipped with a piston (5), comprising an actuating device (7) having a rod-shaped driven member (9) having a structured surface, a control button (8) being movable in axial direction, and a hollow cylindrical counter component (11) having a structured internal sleeve and said counter component matching the rod-shaped driven member (9). When twisting the counter component (11) in relation to the driven member (9), the driven member (9) can be shifted freely in axial direction. This allows the free return of the driving member—without the need for additional control elements—only when the patient releases the driven member (9) by turning it, i.e. by a conscious additional operation.

11 Claims, 4 Drawing Sheets

U.S. PATENT DOCUMENTS

| | | |
|---|---|---|
| 4,946,446 A | 8/1990 | Vadher |
| 4,973,318 A | 11/1990 | Holm et al. |
| 5,017,190 A | 5/1991 | Simon et al. |
| 5,084,060 A | 1/1992 | Freund et al. |
| 5,114,406 A | 5/1992 | Gabriel et al. |
| 5,273,544 A | 12/1993 | Van der Waal |
| 5,279,579 A | 1/1994 | D'Amico |
| 5,279,586 A | 1/1994 | Balkwill |
| 5,292,314 A | 3/1994 | D'Alessio et al. |
| 5,295,976 A | 3/1994 | Harris |
| 5,320,609 A | 6/1994 | Haber et al. |
| 5,336,183 A | 8/1994 | Greelis et al. |
| 5,338,311 A | 8/1994 | Mahukar |
| 5,472,430 A | 12/1995 | Vaillancourt et al. |
| 5,496,293 A | 3/1996 | Huggenberger |
| 5,514,097 A | 5/1996 | Knauer |
| 5,527,294 A | 6/1996 | Weatherford et al. |
| 5,549,558 A | 8/1996 | Martin |
| 5,549,575 A | 8/1996 | Giambattista et al. |
| 5,573,510 A | 11/1996 | Issacson |
| 5,582,598 A | 12/1996 | Chanoch |
| 5,591,136 A | 1/1997 | Gabriel |
| 5,591,138 A | 1/1997 | Vaillancourt |
| 5,609,577 A | 3/1997 | Haber et al. |
| 5,643,214 A | 7/1997 | Marshall et al. |
| 5,658,259 A | 8/1997 | Pearson et al. |
| 5,807,346 A | 9/1998 | Frezza |
| 5,957,897 A | 9/1999 | Jeffrey |

FOREIGN PATENT DOCUMENTS

| | | |
|---|---|---|
| DK | 3645245 | 11/1986 |
| DK | 3900926 | 8/1989 |
| DK | 4223958 | 7/1992 |
| EP | 0037696 | 3/1981 |
| EP | 0058536 | 8/1982 |
| EP | 143895 | 4/1986 |
| EP | 0245312 | 10/1986 |
| EP | 0268191 | 11/1987 |
| EP | 0298067 | 6/1988 |
| EP | B327910 | 1/1989 |
| EP | 0373321 | 6/1990 |
| EP | A496141 | 1/1991 |
| EP | 0516473 | 5/1992 |
| EP | 0498737 | 8/1992 |
| EP | 0554995 | 1/1993 |
| EP | 338806 | 2/1994 |
| EP | 0594349 | 4/1994 |
| EP | 0627229 | 5/1994 |
| EP | 513128 | 7/1995 |
| FR | 2701211 | 8/1994 |
| WO | 8702995 | 5/1987 |
| WO | 9110460 | 7/1991 |
| WO | 9305835 | 8/1992 |
| WO | 9218179 | 10/1992 |
| WO | 9316740 | 9/1993 |
| WO | 9409841 | 5/1994 |
| WO | 9415210 | 7/1994 |
| WO | 9501812 | 1/1995 |
| WO | 9504563 | 2/1995 |
| WO | 9607443 | 3/1996 |
| WO | WO9700091 | 1/1997 |

INJECTION DEVICE FOR INJECTION OF LIQUID

RELATED APPLICATIONS

This application claims the priority of PCT Application No. PCT/CH96/00248, filed Jul. 5, 1996, which is incorporated herein by reference.

The present invention relates to an injection device for injecting fluid according to the preamble of claim 1.

Syringe-shaped injection devices for injecting fluids have been known for some time. They contain a bushing-shaped main body which can be screwed together at approximately the centre and can be divided into two main sections:

a distal section (facing away from the patient) containing the discharge mechanism and comprising at least one rod-shaped driven member having a structured surface (e.g. a screw rod), a hollow cylindrical counter component corresponding to the driven member, provided with a structured internal sleeve (e.g. a screw nut) and a control button; and a proximal section (facing the patient) containing the fluid to be administered and a displaceable piston.

At the proximal end of the main body, a needle and a needle holder are attached, allowing the fluid to be discharged from the device; known needles of this type are for instance PENFINE® needles as described in WO95/01812. The connecting member between the proximal and the distal section of the main body is the driven member, shifting the piston by the selected dose in proximal direction, which causes a discharging of the fluid through the needle.

Often the fluid to be injected is not directly contained in the main body but in an ampoule, with the fluid being stored between a pierceable membrane and a piston displaceable by sliding.

Depending on the injection device, various features are expected from the discharge mechanism. There are devices allowing only a single discharge, devices allowing several discharges of the same dose and devices allowing freely selectable discharges.

For patients using injection devices allowing a change of ampoules, it is—irrespective of the complexity of the discharge mechanism—extremely difficult to wind back the driven member to the initial position in order to make the device ready for operation after the ampoule has been changed. Devices requiring the driven member to be rewound by the control button are known from WO93/16740.

Devices allowing the threaded rod to be pushed back, as in publications U.S. Pat. No. 4,592,745 and EP-A-0 554 995, are more easily operated by patients. The disadvantage of these prior art devices is that due to the release of the distal section from the proximal section of the main body the threaded nut is spread, allowing the threaded rod to move freely without any conscious operation by the patient, with screwing together of both sections of the main body after replacement of the ampoule easily causing a premature unintentional discharge of fluid. Depending on the injection device, this could also result in an incorrect dosing which, in case of certain medication, could prove extremely hazardous to the patient's health.

The invention aims to remedy this situation. It is the object of the invention to provide an injection device in which the sliding back of the driven member requires a conscious operation by the patient, which releases the driven member and counter component from each other to prevent the hazard of an incorrect dosing.

The invention solves the set task with an injection device comprising the characteristics of claim 1.

The advantages achieved by the invention lie mainly in the fact that the free return or free back sliding of the driven member—without the need for additional control elements to be mounted—is only possible when the patient releases the driven member by turning it, i.e. by a conscious additional operation.

A preferred embodiment of the invention is shown in the figures, where:

In the subsequent description the terms proximal and distal are used in their usual medical sense, i.e.

proximal=facing the patient and distal=facing away from the patient.

Figure 1:
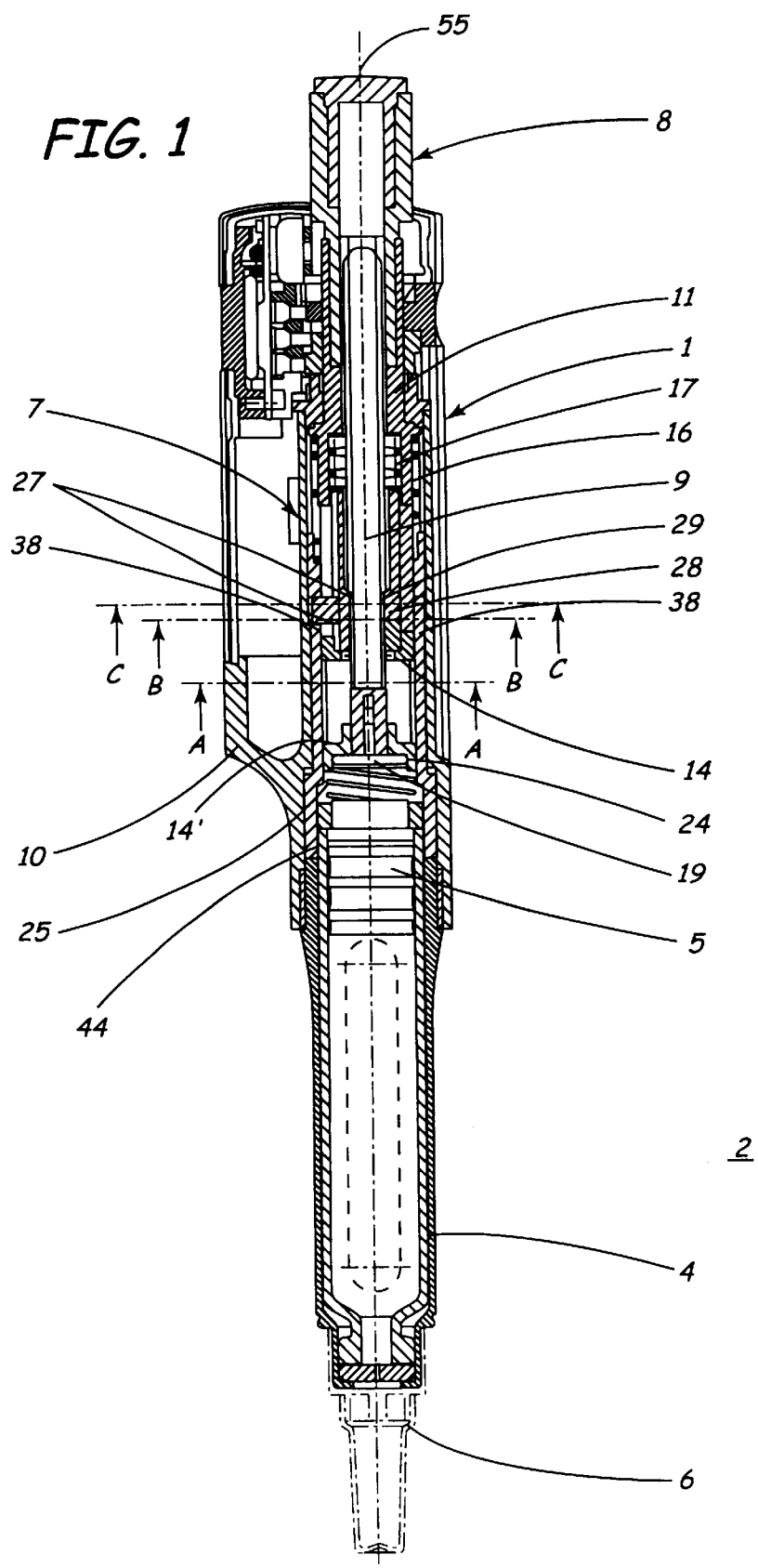
FIG. 1 shows an injection device according to the invention with a retained threaded rod.
Figure 2:
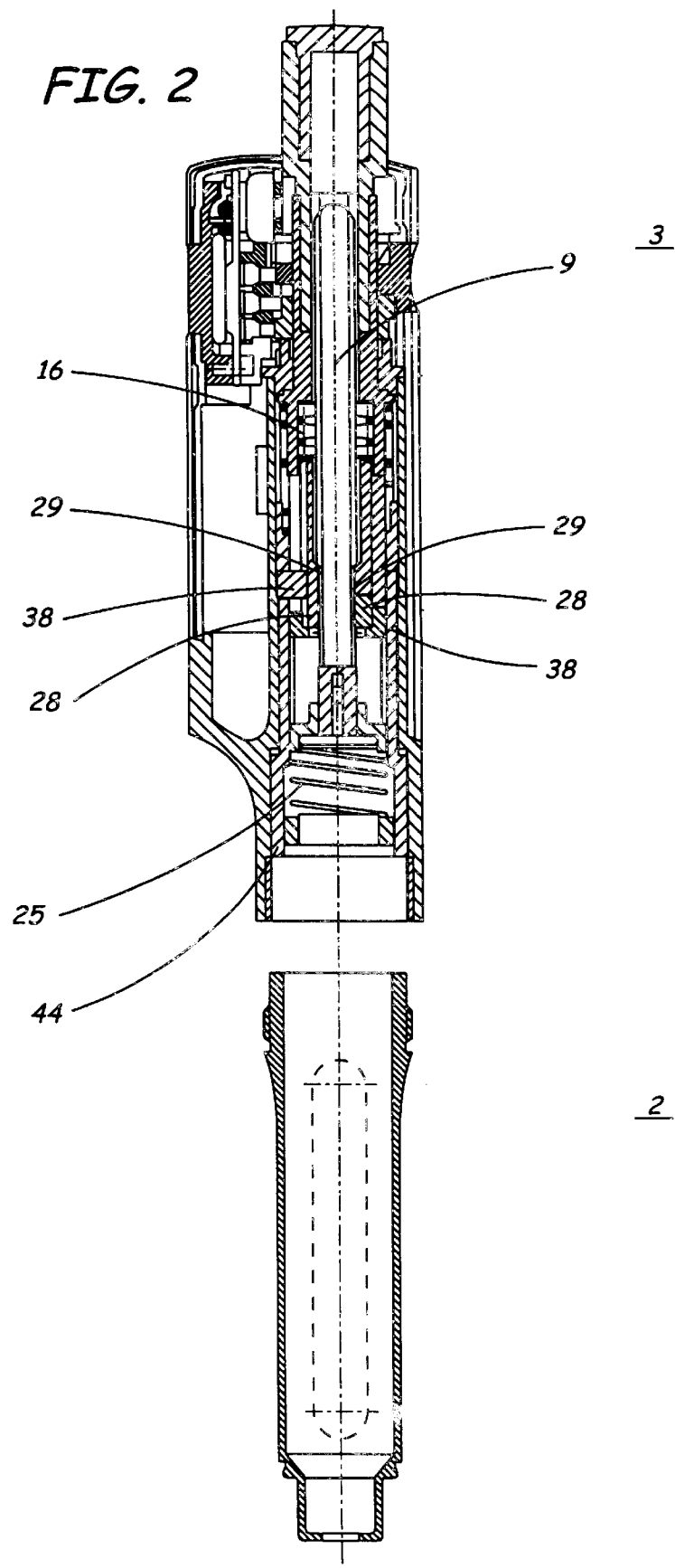
FIG. 2 shows an injection device according to the invention with a threaded rod freely displaceable in longitudinal direction.

As shown in FIG. 1, the injection device according to the invention comprises a bushing-shaped main body 1 which can be divided into a rear (distal) section 3 containing the tubular actuating device or discharge mechanism 7 and a front (proximal) section 2 containing a replacable carpule 4 with a displaceable piston 5. A needle 6 with its distal end connected to the fluid to be discharged can be screwed to the proximal end of the main body 1. The actuating device 7 comprises a control button 8, a rod-shaped driven member 9 in the form of a threaded rod with a flange 19, a guide member 24 and a hollow cylindrical counter component 11 in the form of a driving member.

The tubular driving member 11 is rigidly connected to the control button 8 to prevent twisting. At the proximal end the driving member contains a split threaded nut 27 engaging into the thread of the threaded rod 9. The threaded rod 9 is seated within the driving element 11.

Figure 3:
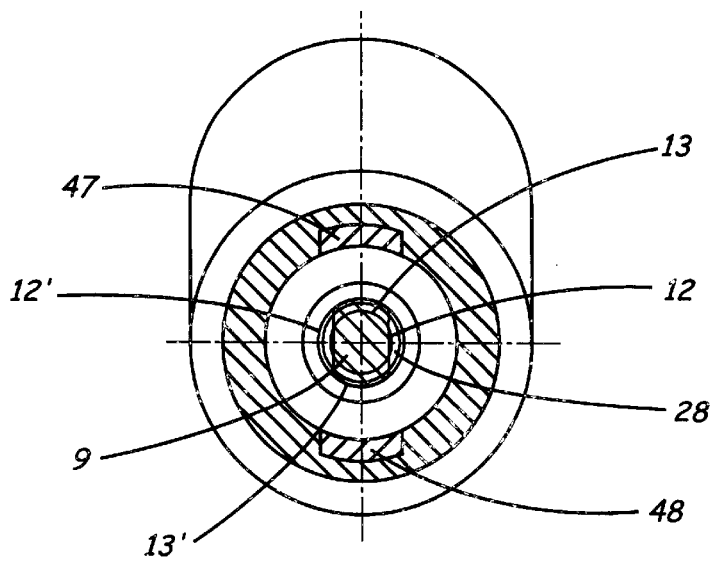
FIG. 3 shows a cross section along line A—A of FIG. 1.
Figure 4:
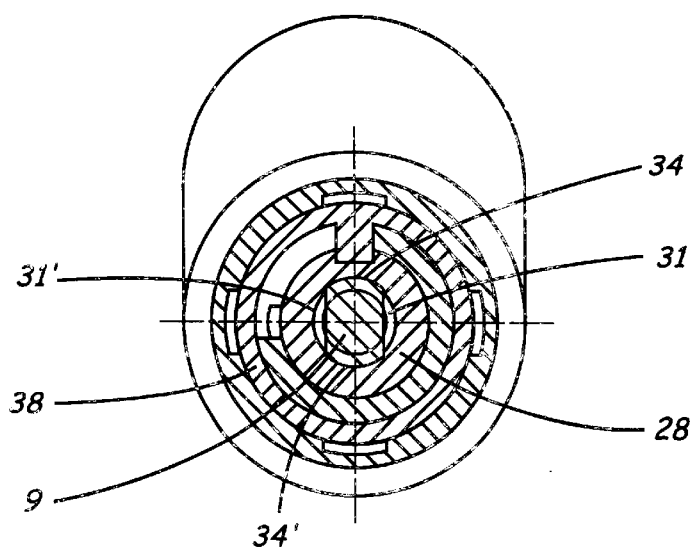
FIG. 4 shows a cross section along line B—B of FIG. 1.
Figure 5:
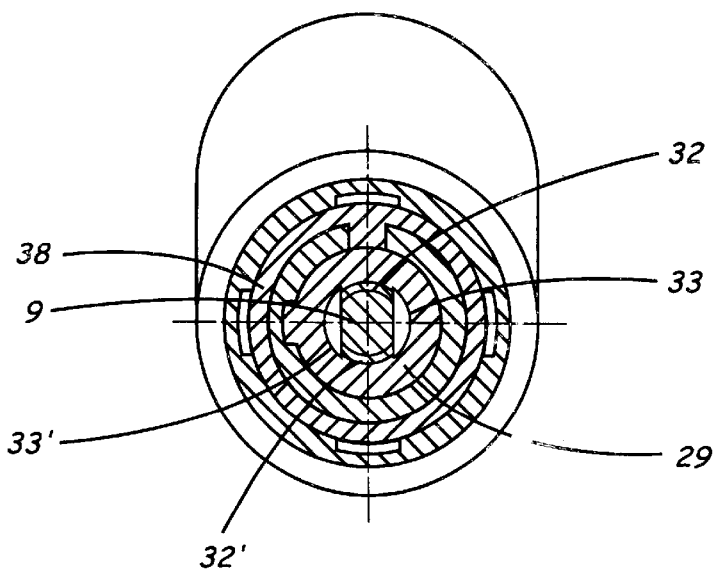
FIG. 5 shows a cross section along line C—C of FIG. 1.

FIG. 3 shows that the threaded rod 9 comprises two opposing level surfaces 12, 12' and apart from that is of a circular cross section with the circular sections 13, 13' being threaded.

The guide member 24 is rigidly connected to the mechanism holder 10 and consequently to the bushing-shaped body 1, thus preventing rotation or axial movement and is positioned in front of the driving member 11. The aperture in the guide member 24, through which the threaded rod 9 passes, is of the same cross section as the threaded rod 9—although enlarged by certain tolerances. As the guide member 24—in contrast to the driving member 11—is not threaded, the threaded rod 9 can be displaced to and fro in axial direction in the aperture of the guide member. A rotational movement of the threaded rod 9 is therefore not possible as the guide member 24 does not allow this.

The control button 8 may be moved in axial direction or may be rotated. If the control button is moved by being pushed in proximal direction, it simultaneously displaces the driving member 11 until its front face 14 pushes against the rear face 14' of the guide member 24.

The threaded rod 9 is connected to the driving member 11 by the threaded segments 31, 31', 32, 32', thus allowing any axial movement of the control button 8 to be transferred. See detailed description of the internal screw thread below.

The axial movement is effected against the bias of a spring 16, returning the actuating device 7 to its home position.

When turning the control button 8 to adjust a dose, the driving member 11 is also turned. This rotating movement is, however, not transferred to the threaded rod 9 as the rod is rigidly seated in the guide member 24. As a result of the rotating threaded nut 27 of the driving member 11, the threaded rod is rigidly driven forward via the threaded segments 31, 31', 32, 32' on the threaded sections 13, 13' of the threaded rod 9 (or backward, when reversing the rotation direction of the control button 8), thus bringing the flange 19 into the position required for the next dose to be discharged, i.e. the distance of the flange 19 from piston 5 is respectively reduced.

By pressing the control button 8, the pre-set dose is discharged. This process is described in detail in WO 93/16740.

If the carpule 4 is empty and the threaded rod 9 is therefore in the extreme proximal position, the threaded rod must be returned to its extreme distal position before a new full carpule 4 can be connected. The injection device 1 according to the invention then allows the threaded rod 9 to be returned. FIGS. 1–5 show that the thread of the driving member 11 is divided horizontally—in relation to the longitudinal axis 55—into two bushing-shaped threaded nut sections 28, 29. The threaded rod 9 can therefore be returned as the threaded sections 13, 13' of the threaded rod 9 engaging into the threaded nut sections are released from the threaded nut sections 28, 29. Each of these threaded nut sections 28, 29 comprises two threaded segments 31, 31', 32, 32' protruding from the level internal surfaces 33, 33', 34, 34'. Always two threaded segments (90°) 31, 31', 32, 32' face each other. Each 90° threaded segment 31, 31', 32, 32' is followed by a 90° level segment 33, 33', 34, 34'. The two threaded nut sections 28, 29 are offset by angle of 900 when operational, so that the threaded rod 9 is completely surrounded by threaded surfaces on all sides. The external thread of the threaded rod 9 therefore engages at times only with two threaded segments of one or the other threaded nut section. As shown below, the fact that only two threaded segments engage in the external thread of the threaded rod is fundamental for allowing the threaded rod to be returned.

Figure 6:
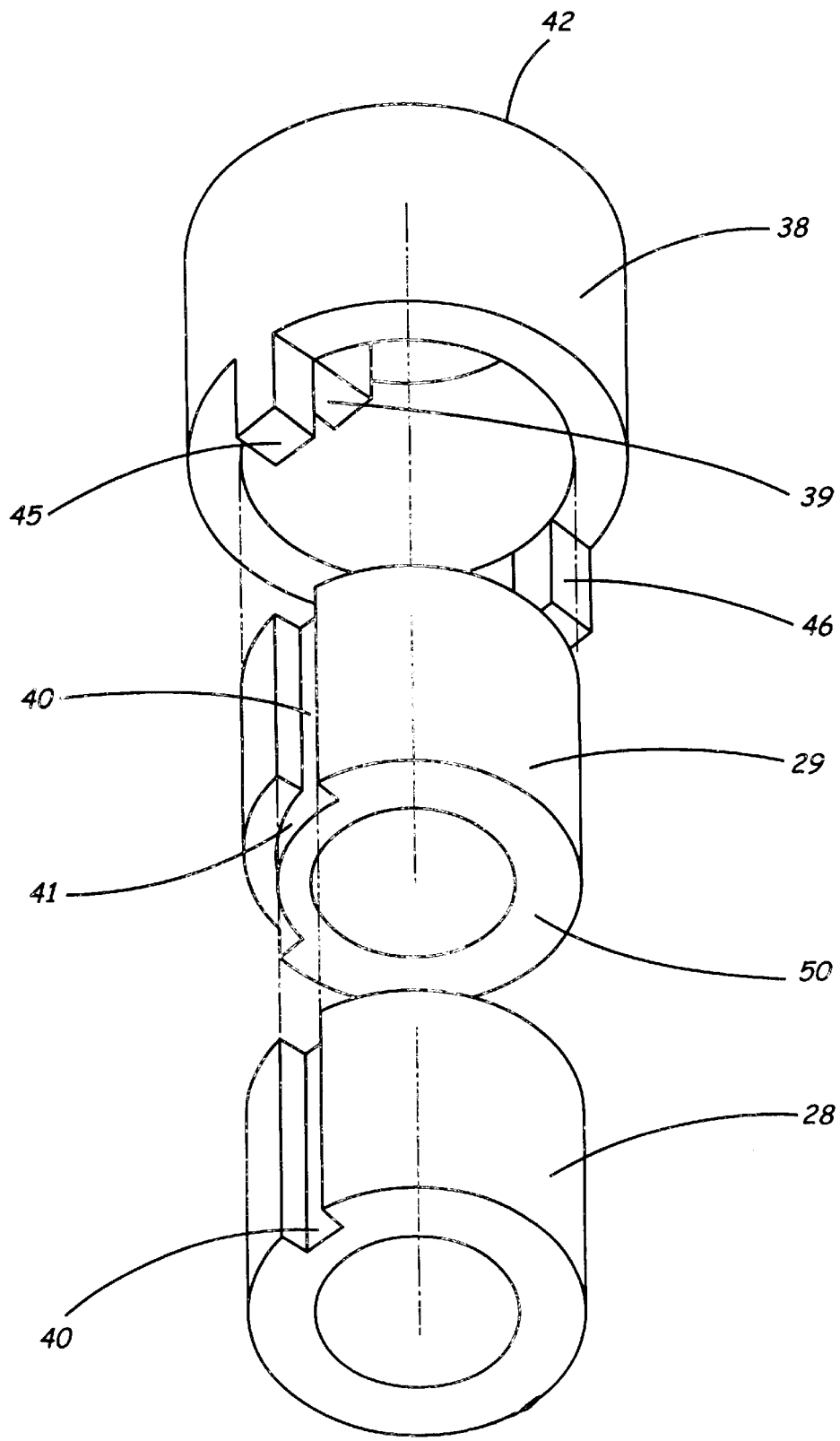
FIG. 6 shows a coupling bushing for the injection device according to the invention.

Both bushing-shaped threaded nut sections 28, 29 are surrounded by a bushing-shaped coupling member 38. The internal diameter of the coupling member 38 corresponds thereby to the external diameter of the threaded nut sections 28, 29 so that the coupling member 38 can slide over the threaded nut sections. FIG. 6 shows that the coupling member contains an internal cam 39 engaging in an indentation 40 in the external surfaces of the threaded nut sections 28, 29.

The distal threaded nut section 29 is rigidly connected with the driving member 11 so that each rotational movement of the driving member is directly transferred to the distal threaded nut section 29. The movement is transferred to the proximal threaded nut section 28 via coupling member 38. Any axial movement of the driving element 11 is transferred to both threaded nut sections 28, 29 via the spring 17.

The coupling member 38 can be axially shifted between a proximal and a distal position. The distal position corresponds to the operating position shown in FIG. 1 and the proximal position to the position shown in FIG. 2. As detailed below, the threaded rod may also in the position shown in FIG. 2 still be retained by the distal threaded nut.

When the coupling member 38 is in its distal position, the two threaded nut sections 28, 29 are coupled and offset at an angle of 90° and the threaded rod is therefore surrounded by threaded surfaces on all sides. When, however, the coupling member 38 is in its proximal position both threaded nut sections 28, 29 can be rotated by 90°, i.e. are releasable from the threaded rod 9.

In order to allow the rotation of both threaded nut sections 28, 29 in the proximal position of the coupling member 38, the distal threaded nut section 29 contains an indentation 41 in its proximal face 50, extending vertically in relation to indentation 40. When the coupling member 38 is in the proximal position, the rear face 42 and consequently the internal cam 39 are positioned in the indentation 41 of the distal threaded nut section 29, thus allowing the distal threaded nut section 29 to be rotated by 90° in relation to the proximal threaded nut section 28.

The change of position of the coupling member 38 is effected by the slide 44. When the slide 44 and the coupling member 38 are in the distal position (FIG. 1) two cams 45, 46 attached to the proximal face 43 of the coupling member 38 are in contact with the mechanism holder 10. The mechanism holder contains two apertures filled by two elongations of the slide 44, thus preventing both cams 45, 46 from sliding to the proximal position. Both apertures 47, 48 are arranged in such a way that the coupling bushing 38 can only slide into the proximal position when the threaded nut segments 31, 31' of the proximal threaded nut section 28 are not engaged in the threaded rod 9.

When the two main sections 2, 3 of the main body 1 are separated (FIG. 2), the pressure of the spring 16 shifts the slide 44 into its front stop via the coupling bushing 38, when both cams 45, 46 of the coupling bushing 38 are positioned over the apertures 47, 48 of the mechanism holder 10. The coupling bushing 38 can only slide into its proximal position and simultaneously shift the slide 44 in proximal direction when both cams 45, 46 of the coupling bushing 38 are positioned over the apertures 47, 48 of the mechanism holder 10. When the slide 44 and the coupling bushing are in the proximal position, a 90° rotation of the control button 8 against the normal dosing direction causes the distal threaded nut section 29 to be rotated by 90°, i.e. causes both threaded nut sections 28, 29 to be arranged behind each other in the same position. In this position none of the threaded nut sections 31, 31', 32, 32' are in contact with the thread of the threaded rod 9 and therefore the threaded rod can be freely shifted.

When both main sections 2, 3 are joined and both threaded nut sections 28, 29 have been rotated by 90°—i.e. are rigidly engaged in the threaded rod 9—the slide 44 can be shifted in distal direction, simultaneously shifting the coupling member 38 in distal direction as the internal cam 39 of the coupling bushing 38 can slide in, the indentation 40 of both threaded nut sections 28, 29.

When both threaded nut sections have, however, not been rotated by 90° and it is nevertheless attempted to join both main sections 2,3, the slide 44 cannot be shifted in distal direction as the internal cam 39 of the coupling bushing 38 is positioned in the indentation 41 of the distal threaded nut section 29. It is therefore not possible, with the two threaded nut sections 28, 29 in this position, to completely join both main sections 2, 3. In order to draw the patient's attention to the fact that the injection device is not operational, the part of the two main sections normally not visible, but remaining visible due to the incomplete joining, can be coated with a striking colour.

By rotating the control button 8 in the operating direction, the internal cam 39 of the coupling member 38 is rotated out of the horizontal indentation 41 of the distal threaded nut section 29 and into its vertical indentation 40. In this position, the coupling bushing 38 can be shifted by slide 44 into the operating position.

More simple driving mechanisms could also be imagined, in which a simple rotation of the rod-shaped driven member 9 or of the associated counter component 11 allows the free return of the rod-shaped driven member. The driven member 9 can also contain a saw-tooth-like structure with a respective counter component 11. For this purpose, it is immaterial whether the rotational movement is carried out on the control button or on the main body, for instance at the distal section 3.

What is claimed is:

1. An injection device having a longitudinal axis for injecting fluid from a fluid container equipped with a piston, comprising an actuating device having a rod-shaped driven member having a first engagement surface, a control button being movable in an axial direction and a hollow cylindrical counter component having a second engagement surface, said counter component being substantially coaxially arranged in relation to said driven member and generally surrounding at least a portion of said driven member, said counter component comprising a bushing-shaped nut being radially split generally orthogonally with respect to the longitudinal axis of the injection device, said bushing-shaped nut being releasibly engaged to said rod-shaped driven member, and said bushing-shaped nut being twistable by a user to a position that releases said driven member from said nut so that said driven member is freely shiftable in an axial direction.

2. The injection device of claim 1, wherein the bushing-shaped nut comprises a proximal section and a distal section.

3. The injection device of claim 2, wherein both sections of the bushing-shaped nut comprise an indentation in the external surface substantially parallel to the longitudinal axis of the injection device, and wherein the distal nut section comprises an indentation substantially transverse to the longitudinal axis of the injection device extending along a portion of the bushing circumference at its proximal edge.

4. The injection device of claim 3, wherein both sections of the bushing-shaped nut are slidably connected to a bushing-shaped coupling member, wherein the bushing-shaped coupling member includes an internal cam having a rear edge that is in proximal position of the coupling, and that is slidably connected with the substantially transverse indentation of the distal threaded-nut section.

5. The injection device of claim 4, wherein the bushing-shaped coupling remember is axially shiftable between a proximal position and a distal position, and wherein the driven member must be in a slidable relationship with the counter component before the coupling member is shifted to the proximal position.

6. The injection device of claim 5, wherein said free shiftability of said driven member occurs independently of any movement of said fluid container.

7. The injection device of claim 6, wherein said twisting of said bushing-shaped nut occurs independently of any movement of said fluid container.

8. An apparatus for injecting fluid having a longitudinal axis, comprising:

a piston slidably engaged with a fluid container;

a driven member;

a counter component comprising a proximal bushing-shaped nut and a distal bushing-shaped nut, the proximal bushing-shaped nut being coaxial with and rotatable relative to the distal bushing-shaped nut wherein said proximal bushing-shaped nut and said distal bushing-shaped nut are divided along a plane that is generally orthogonal with respect to the longitudinal axis; and a coupling member adapted to rotate the proximal bushing-shaped nut relative to the distal bushing-shaped nut from a first orientation in which the proximal bushing-shaped nut and the distal bushing-shaped nut cooperate to threadably engage the driven member to a second orientation in which the proximal bushing-shaped nut and the distal bushing-shaped nut cooperate to allow the driven member to slide freely in an axial direction relative to die counter component; and a control button operably connected to the counter component, wherein any rotation of the proximal bushing-shaped nut requires a physical manipulation of the control by a user.

9. The injection device of claim 8, wherein the proximal bushing-shaped nut and the distal bushing-shaped nut comprise a plurality of radially spaced threaded sections.

10. The injection device of claim 8, wherein the driven member comprises a plurality of radially spaced threaded sections.

11. The injection device of claim 8, wherein said rotation of said proximal bushing-shaped nut occurs independently of any movement of said fluid container.

* * * * *

UNITED STATES PATENT AND TRADEMARK OFFICE
CERTIFICATE OF CORRECTION

PATENT NO.   : 6,413,242 B1
DATED        : July 2, 2002
INVENTOR(S)  : Peter Michel, Peter Nydegger and Philipp Weber It is certified that error appears in the above-identified patent and that said Letters Patent is hereby corrected as shown below:

Column 3,
Line 35, please delete "900" and insert -- 90° -- therefor.

Column 5,
Line 48, please delete "remember" and insert -- member -- therefor.

Signed and Sealed this

Twenty-sixth Day of November, 2002

Attest:

Attesting Officer

JAMES E. ROGAN
*Director of the United States Patent and Trademark Office*